United States Patent [19]

Kawakami et al.

[11] 4,251,651

[45] Feb. 17, 1981

[54] AMPHOTERIC POLYELECTROLYTE

[75] Inventors: Shigenao Kawakami, Osaka; Shigeru Ura, Saitama; Naoyoshi Jinno; Shin-Ichi Isaoka, both of Osaka; Wataru Tohoma, Saitama, all of Japan

[73] Assignee: Sumitomo Chemical Company, Limited, Osaka, Japan

[21] Appl. No.: 907,854

[22] Filed: May 19, 1978

[30] Foreign Application Priority Data

May 31, 1977 [JP] Japan ................... 52-64216

[51] Int. Cl.$^3$ ................... C08F 214/00; C08F 214/14
[52] U.S. Cl. ................... 526/204; 162/164 R; 526/208; 526/212; 526/217; 526/218; 526/229; 526/232.1; 526/240; 526/292
[58] Field of Search ............... 526/240, 292, 204, 208, 526/212, 217, 218, 229, 232.1

[56] References Cited

U.S. PATENT DOCUMENTS

| 3,658,771 | 4/1972 | Volk et al. | 526/240 |
|---|---|---|---|
| 3,843,585 | 10/1974 | Kangas et al. | 526/292 |
| 3,901,857 | 8/1975 | Sackmann et al. | 526/292 |
| 3,907,758 | 8/1975 | Sackmann et al. | 526/292 |
| 4,075,183 | 2/1978 | Kawakami et al. | 526/292 |
| 4,111,922 | 9/1978 | Beede | 526/292 |
| 4,115,339 | 9/1978 | Restaino | 526/292 |
| 4,138,446 | 2/1979 | Kawakami et al. | 526/292 |

*Primary Examiner*—Harry Wong, Jr.
*Attorney, Agent, or Firm*—Birch, Stewart, Kolasch & Birch

[57] ABSTRACT

An amphoteric polyelectrolyte which is useful as a paper additive capable of imparting dry strength to paper, a high molecular flocculant, a high molecular dehydrating agent or the like is prepared by copolymerizing a cationic vinyl monomer such as β-methacryloxyethyl trimethylammonium chloride, an anionic vinyl monomer such as acrylic acid and a vinyl monomer such as acrylamide, optionally with a nonionic vinyl monomer such as acrylonitrile, in a solvent in the presence of a catalyst.

8 Claims, No Drawings

AMPHOTERIC POLYELECTROLYTE

The present invention relates to an amphoteric polyelectrolyte, and its production and use. More particularly, it relates to a novel amphoteric polyelectrolyte, a process for preparing such amphoteric polyelectrolyte, and a paper additive, a high molecular flocculant or a high molecular dehydrating agent containing such amphoteric polyelectrolyte.

Since amphoteric polyelectrolytes have both a cationic group and an anionic group in the same polymer molecule, they have an isoelectric region corresponding to an isoelectric point which is a characteristic of common amphoteric electrolytes. From the change of the viscosity of their aqueous solutions, it is assumed that the state of the polymer chain in an aqueous solution is different when in and out of the isoelectric region; i.e. in the isoelectric region, the chain is in a less extended state while out of this region, it is in an extended state. These two forms may be changed reversibly by adjusting the pH of the aqueous solution. Further, amphoteric polyelectrolytes possess both the characteristics of polymers having cationic groups alone and those of polymers having anionic groups alone.

Based on the above characteristics, amphoteric polyelectrolytes are widely used. For example, they may be used as antistatic agents for synthetic fibers, synthetic resin films, molded products, fuel oils and the like, electro-conductive agents for electrostatic recording paper, facsimile paper and the like, retention aids, paper additives, sizing agents, high molecular flocculants, dehydrating agents, decoloring agents for various kinds of colored waste water such as waste water from dyeing works, adsorption resins for heavy metals, ion-exchange resins, components of cosmetics such as hair sprays and setting lotions, antirust agents, fungicides, anti-mold agents, anti-clouding agents and the like.

The amphoteric polyelectrolytes of the invention are characteristic in that they display the properties as amphoteric polyelectrolytes even in the presence of various ions or surface active agents, in addition to the aforesaid fundamental properties inherent to the common amphoteric polyelectrolytes. Such characteristic feature is particularly remarkable when a nonionic vinyl monomer is used as a starting material, and this is a great feature which has never been observed with conventional cationic, anionic or amphoteric polyelectrolytes.

In the paper-making industry or the water treatment industry, there is a strong demand for development of paper additives, high molecular flocculants and high molecular dehydrating agents which act effectively even in the presence of various ions or surface active agents. The amphoteric polyelectrolytes of the invention are of important significance in meeting these demands.

The amphoteric polyelectrolytes of the invention are very useful for various purposes as described hereinbefore, and they are particularly useful as paper additives, high molecular flocculants and high molecular dehydrating agents.

The amphoteric polyelectrolytes of the invention can be prepared by copolymerization of a vinyl monomer of the formula:

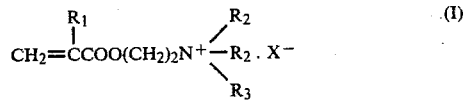

wherein $R_1$ is a hydrogen atom or a methyl group, $R_2$ and $R_3$ are each a methyl group or ethyl group and X is a chlorine atom, a bromine atom or an iodine atom, a vinyl monomer of the formula:

wherein M is a hydrogen atom, an alkali metal atom or an ammonium group and $R_4$ is a hydrogen atom or a methyl group and a vinyl monomer of the formula:

wherein $R_5$ is a hydrogen atom or a methyl group, optionally with a vinyl monomer of the formula:

wherein $R_6$ is a hydrogen atom or a methyl group and $R_7$ is a phenyl group, —CN or —COOR$_8$ (in which $R_8$ is methyl, ethyl, phenyl or —(CH$_2$)$_n$OH wherein n is 2 or 3).

The vinyl monomer (I) may be a quaternary ammonium group-containing vinyl monomer produced by quaternizing a dialkylaminoalkyl ester of acrylic acid or methacrylic acid with an alkyl halide. Specific examples of the vinyl monomer (I) include quaternized products resulting from dimethylaminoethyl acrylate, diethylaminoethyl acrylate, dimethylaminoethyl methacrylate, diethylaminoethyl methacrylate, etc. As the quaternizing agent, there may be exemplified methyl chloride, methyl bromide, methyl iodide, ethyl bromide, etc. Of these, the products quaternized with methyl chloride are preferably used for the purposes of the present invention.

The use of the vinyl monomer (I) is one of the characteristic features of the invention. For preparation of amphoteric polyelectrolytes, there have been reported the use of diethylaminoethyl methacrylate [J.A.C.S., 74, 438, (1952)] and of dimethylaminoethyl methacrylate hydrochloride [U.S. Pat. No. 3,843,535] as the cationic component. Since, however, these esters are low in cationic strength and are easily hydrolyzable, they are unsatisfactory in terms of performance and stability. In order to enhance the cationic strength of those esters, their quaternization with conventional quaternizing agents has been attempted. However, the use of dialkyl sulfates well known as quaternizing agents is not only unsatisfactory in safety but also very inferior in stability of the starting monomers and the produced polymer. Moreover, the polymer obtained by the use of such quaternized products is inferior in performances. In contrast to this, alkyl halides, particularly methyl chloride, have been found to be excellent quaternizing agents in affording high stability and good performances of the resulting products.

The vinyl monomer (II) may be a free or salified carboxyl group-containing vinyl monomer, of which examples are acrylic acid and methacrylic acid, and alkali metal salts (e.g. sodium salt, potassium salt) and ammonium salts thereof. Advantageously, these are highly polymerizable and available at a low cost. In addition, they can provide excellent performances to the resulting polymer.

The vinyl monomer (III) includes acrylamide and methacrylamide. These monomers are effective in increasing the molecular weight of the resulting polymer due to its high polymerizability. They are also effective in improving the water solubility of the produced polymer.

The vinyl monomer (IV) specifically includes methyl acrylate, methyl methacrylate, ethyl acrylate, ethyl methacrylate, acrylonitrile, methacrylonitrile, styrene, α-methylstyrene, hydroxyethyl acrylate, hydroxyethyl methacrylate, hydroxypropyl acrylate, hydroxypropyl methacrylate and the like. The use of methyl acrylate, methyl methacrylate or acrylonitrile is particularly preferred. The vinyl monomer (IV) is an optional component in the present invention, but in some cases the performances of the produced polymer can be much enhanced by incorporating the vinyl monomer (IV) therein. For instance, exertion of the valuable effect in the presence of various ions or surface active agents is made more remarkable when the units of the vinyl monomer (IV), particularly of methyl acrylate, methyl methacrylate or acrylonitrile, are present in the polymer.

The proportion of the vinyl monomers to be copolymerized may be varied depending on the desired properties of the resulting polymer, the kinds of monomers used, the polymerization mode to be adopted, etc. But, the molar proportion of the vinyl monomers (I), (II), (III) and (IV) is usually about 1 to 85:1 to 85:5 to 98:0 to 50, preferably about 2 to 85:2 to 85:10 to 96:10 to 30. When the vinyl monomer (I) or (II) is used in an amount less than the said lower limit, the resulting polymer loses the feature as an amphoteric polyelectrolyte. When the amount of the vinyl monomer (III) is less than the said lower limit, the resulting polymer can not have a proper molecular weight. When the amount of the vinyl monomer (IV) is more than the said higher limit, the produced polymer can not retain a proper water solubility and a suitable molecular weight. While the proportion of the vinyl monomers may properly be changed within the aforesaid ranges according to the use, a molar ratio of the vinyl monomer (I) to the vinyl monomer (II) is usually from 1:10 to 10:1, preferably from 1:4 to 4:1.

The copolymerization of the vinyl monomers may be carried out in an aqueous medium in the presence of a catalyst by a per se conventional procedure such as solution polymerization, emulsion polymerization or precipitation polymerization.

In case of solution polymerization, there may be employed as the reaction medium water, a lower alkanol or their mixture, among which the use of water is particularly preferred. The total concentration of the vinyl monomers in the aqueous medium may be from about 5 to 80% by weight. Depending on the total concentration or composition of the vinyl monomers, the polymer is produced in a form ranging from a fluidizable liquid to a non-fluidizable solid. When the product is a liquid, it may be used as such. When the product is a solid, it may be crushed, if necessary, followed by drying to give a powdery material.

The amphoteric polyelectrolyte of the invention can be obtained in a powdery form by effecting the copolymerization in a mixture of water and a water-miscible organic solvent. In this case, the organic solvent concentration of the solvent system is adjusted to be from 15 to 70% by weight, and the reaction is carried out at a temperature below the boiling point of the solvent system. A typical example of the favorable operations is as follows: a part of the feed amount of the vinyl monomer (I) is admixed with a mixture of water and a water-miscible organic solvent, and all the feed amounts of the vinyl monomers (II) and (III), or of the vinyl monomers (II), (III) and (IV) are added thereto; copolymerization is started by the addition of a polymerization initiator thereto; and the rest of the vinyl monomer (I) is added to the reaction system to allow the reaction to further proceed, during which the viscosity of the system is controlled by addition of the water-miscible organic solvent. Thus, products of high molecular weight are obtainable. As the water-miscible organic solvent, there may be employed a lower alcohol acetone, acetonitrile, dioxane and the like, among which acetone is particularly preferred.

The molecular weight of the polymer can be determined depending upon the purposes of use, as is well known, by proper selection of reaction conditions such as monomer concentration, catalyst concentration and reaction temperature. In practice, the reaction conditions are selected so as to give the Brookfield viscosity (25° C., rotor No. 3) of the polymer in a 10% by weight aqueous solution of 1 poise or more. As the catalyst used herein, benzoyl peroxide, azoisobutyronitrile, ammonium persulfate, potassium persulfate, hydrogen peroxide and the like are effective. Also, conventional redox catalysts comprising, for example, potassium persulfate and any one of sodium hydrogen sulfite, tertiary amines and sodium formaldehyde sulfoxylate are effective. The catalyst is used in an amount of 0.01 to 1.0% by weight based on the total weight of the vinyl monomers.

The amphoteric polyelectrolyte of the invention is highly effective in imparting dry strength to paper.

As is well known, an increase in the dry strength of paper has so far been achieved by the so-called beater addition method or by other methods. The former method is intended to reinforce bonding between fibers using chemicals, and comprises adding chemicals (e.g. starches, vegetable gums, water soluble synthetic resins) to a pulp or fiber slurry thereby allowing the chemicals to be adsorbed thereon, followed by sheeting and drying. As the latter methods, the chemicals are sprayed onto webs at the sheeting step or base papers after sheeting, or the webs or the base papers are impregnated with the chemicals.

As the chemicals used for this purpose, there have been developed various water soluble resins such as anionic polyacrylamides obtained by copolymerizing acrylamide and acrylic acid or a salt thereof, and cationic polyacrylamides such as copolymers of acrylamide and a cationic vinyl monomer, Mannich reaction products of polyacrylamide and Hoffman degradation products of polyacrylamide. The former anionic polyacrylamides are generally used together with cationic chemicals such as alum to allow them to be adsorbed onto anionic pulp fibers. The latter cationic materials are generally adsorbed onto pulp without a fixing agent and display a processing effect.

Recently, however, there is an increasing tendency for service water to be used in circulation on account of problems of environmental pollution and shortage of service water, and washing of the pulp tends to be omitted. As a result, large amounts of black liquor and various organic or inorganic salts enter the service water and accumulate, and therefore there appears the tendency that the effect of the aforesaid anionic or cationic paper additives is largely lowered. Consequently, there has been a strong demand for effective paper additives.

Amphoteric polyelectrolytes are considered as being sufficiently effective to meet these demands, but conventional amphoteric polyelectrolytes are not yet satisfactory in terms of performances and stability.

The features of the amphoteric polyelectrolyte of this invention as a paper additive are very superior in the following points:

(1) The dry strength imparting effect is very high;
(2) The increase of wet strength is low without lowering the repulping of broke;
(3) The effect is high even in the presence of miscellaneous ions; and
(4) Stability is high.

In a commercial use of the amphoteric polyelectrolyte of the invention as a paper additive, the so-called beater addition method or other procedures are employed. The former method comprises adding the polyelectrolyte to an aqueous suspension liquor of cellulose pulp fibers thereby allowing the polyelectrolyte to be adsorbed onto the fibers, followed by sheeting and drying. As to the latter ones, the polyelectrolyte is sprayed onto paper by means of a spray, or paper is impregnated therewith by means of a size press. In general, the beater addition method is more frequently used. In this case, the amount of the polyelectrolyte added depends upon the kind of paper and required strength, but generally it is within the range of from 0.05 to 5% by weight (converted to dry basis) based on the dry weight of the paper. More favorably, a sufficient dry strength imparting effect is obtained within the range of from 0.1 to 2% by weight.

Also, the amphoteric polyelectrolyte of the invention displays a very high effect as an amphoteric high molecular flocculant or a high molecular dehydrating agent which is effective for separation of suspended solids in an aqueous medium by flocculation or dehydration of the solids by filtration.

As flocculants for such purposes, various high molecular flocculants are developed and used in practice. For example, there can be mentioned neutral polyelectrolytes such as polyacrylamide and polyethylene oxide, anionic polyelectrolytes such as partial hydrolyzed polyacrylamide, copolymers of acrylamide and acrylic acid and polyacrylic acid, and cationic polyelectrolytes such as Mannich modification products of polyacrylamide, polyimidazoline, polydialkylaminoalkyl acrylate and polydialkylaminoalkyl methacrylate. These conventional polyelectrolytes are effectively used according to their respective features, which however means that uses of these polyelectrolytes are limited.

For example, in waste water treatment with partial hydrolyzed polyacrylamide or copolymers of acrylamide and acrylic acid, it is necessary to properly apply these polymers according to the pH level of waste water. That is, waste water of high pH is treated with the polymers of high anionic strength and waste water of low pH with those of low anionic strength. It is therefore necessary to know the property of the waste water in advance. Further, referring to flocculation-separation of suspension liquors with conventional high molecular flocculants, anionic flocculants are superior in a flocculated product-depositing effect but are inferior in a waste water-clarifying effect. While, in the case of cationic ones, the latter effect is superior but the rate at which flocculated products are deposited is low.

For improving these drawbacks, there is a method of using a synergistic effect resulting from the combined use of cationic high molecular flocculants and anionic ones. But, the practice of this method is limited. For example, when a cationic flocculant and an anionic flocculant are dissolved together in the same vessel, there are immediately produced useless white gel-like products which no longer act as a flocculant effectively. Consequently, when a cationic flocculant and an anionic flocculant are used together, it becomes necessary to prepare dissolution vessels for the respective flocculants and to determine which of the two is first to be added to waste water. Further, development of a synergistic effect is not necessarily certain. And, one of the greatest drawbacks of conventional high molecular flocculants is that the effect as flocculants is lowered or lost completely when the waste water contains various ions or surface active agents.

Another drawback of conventional flocculants is that flocs once produced are easily broken by mechanical forces such as stirring. In the case of filtrationdehydration treatment, similarly, conventional flocculants show the following drawbacks: dehydration ability is lowered when waste water contains various ions or surface active agents; and produced flocs are easily broken because of their poor mechanical strengths when vacuum filtration or centrifugal dehydration is applied thereto.

The amphoteric polyelectrolytes of this invention can be used as high molecular flocculants which are not affected by the pH level of waste water and various ions or surface active agents, and which combine the characteristics of anionic high molecular flocculants and those of cationic ones.

In the following examples, flocculation treatment and dehydration treatment with the amphoteric polyelectrolytes of this invention will be explained. In carrying out these treatments, no special equipment or methods are required and, like the treatments with conventional flocculants, the polyelectrolyte is properly diluted with water to obtain a polymer solution, and th polymer solution is added to a suspension liquor to be treated and, after thorough stirring, the mixed liquor is supplied to a flocculation-separation step or filtration-dehydration step. The amount of the polymer solution added is generally within the range of from 0.001 to 5% by weight (converted to the effective components of the amphoteric polyelectrolyte) based on the solid content of the suspension liquors. But the amount is properly varied depending upon the state of the suspension liquors and treatment conditions without being limited to the abovementioned ranges.

The present invention will be illustrated in more detail with reference to the following Examples wherein % is by weight unless otherwise indicated.

EXAMPLE 1

14.0 g of a quaternized product resulting from dimethylaminoethyl methacrylate and methyl chloride (hereinafter referred to as "DAM-CH$_3$Cl"), 5.0 g of acrylic acid (hereinafter referred to as "AA"), 41.0 g of acrylamide (hereinafter referred to as "AM") and 540 g of water were mixed and adjusted to a pH of 4 with 10 N sodium hydroxide. The mixture was placed in a reactor equipped with a stirrer, and the atmosphere in the reactor was replaced by nitrogen gas until it became oxygen-free completely. After adding 0.3 g of potassium persulfate, polymerization was carried out at 80° C. for 3 hours to give a polymer solution. Conversion was 99% or more.

The properties of the polymer solution were as follows: polymer content, about 10%; pH, 3.5; Brookfield viscosity (rotor No. 3; rotation, 12 rpm; 25° C.), 20 ps. The polymer solution may be used as it is, or the polymer may be isolated as a powder by adding an organic solvent such as acetone to the polymer solution, thereby depositing the polymer.

Stability with the lapse of time of this polymer solution was examined by placing the polymer solution in a constant temperature vessel of 50° C., but no change was observed over three months or more.

EXAMPLE 2

Various polymers were produced in the same manner as in Example 1 but varying the monomer composition. The viscosity, isoelectric region and storage stability (at 50° C.) of the product are shown in Table 1.

TABLE 1

| Run No. | DAM—CH$_3$Cl (mol %) | AA (mol %) | AM (mol %) | Viscosity at 25° C. (ps) | Isoelectric region (pH) | Thermal stability at 50° C. |
|---|---|---|---|---|---|---|
| 1 | 10 | 10 | 80 | 40 | 6-8 | Stable over 3 months or more |
| 2 | 2 | 2 | 96 | 45 | 6-7 | |
| 3 | 5 | 5 | 90 | 42 | 6-7 | |
| 4 | 20 | 20 | 60 | 40 | 6-8 | |
| 5 | 2 | 8 | 90 | 20 | 4-5 | |
| 6 | 15 | 5 | 80 | 40 | 8-10 | |
| 7 | 25 | 25 | 50 | 35 | 6-9 | |

EXAMPLE 3

A mixture of 20.0 g of DAM-CH$_3$Cl, 7.0 g of AA, 10.0 g of acrylonitrile (hereinafter referred to a as "AN"), 41.5 g of AM and 706 g of water was adjusted to pH of 4 with 10 N sodium hydroxide and placed in a reactor equipped with a stirrer. After removing oxygen, 0.4 g of potassium persulfate was added, and polymerization was carried out at 70° C. for 4 hours to give a polymer solution. Conversion was 99.6%. The properties of the polymer solution were as follows: polymer content, 10%; pH, 3.6; Brookfield viscosity, 30 ps. From this polymer solution, a powder was obtained in the same manner as in Example 1.

EXAMPLE 4

Various polymers were produced in the same manner as in Example 3 but varying the monomer compositions as shown in Table 2. The physical properties of the product are shown in Table 2.

TABLE 2

| Run No. | DAM—CH$_3$Cl (mol %) | AA (mol %) | AN (mol %) | MA (mol %) | MMA (mol %) | HEMA (mol %) | ST (mol %) | AM (mol %) | Viscosity at 25° C. (ps) | Isoelectric resion (pH) | Thermal stability at 50° C. |
|---|---|---|---|---|---|---|---|---|---|---|---|
| 8 | 10 | 10 | 20 | — | — | — | — | 60 | 45 | 6-8 | Stable over 3 months or more |
| 9 | 10 | 10 | 35 | — | — | — | — | 45 | 52 | 6-8 | |
| 10 | 10 | 10 | 10 | — | 5 | — | — | — | 75 | 40 | 6-8 | |
| 11 | 10 | 10 | — | — | 5 | — | — | 75 | 40 | 6-8 | |
| 12 | 10 | 10 | — | — | — | 10 | — | 70 | 45 | 6-8 | |
| 13 | 10 | 10 | — | — | — | 30 | — | 50 | 50 | 6-8 | |
| 14 | 10 | 10 | — | — | — | — | 5 | 75 | 40 | 6-8 | |

Note:
Ma: methyl acrylate; MMA: methyl methacrylate; HEMA: hydroxyethyl methacrylate; ST: styrene

Reference Example 1

Various polymers were produced in the same manner as in Example 1 or 3 but varying the monomeric compositions as shown in Table 3. The physical properties of the polymers are shown in Table 3. The stability of the polymers with DAM-HCl, DAM-H$_2$SO$_4$ and DAM-(CH$_3$)$_2$SO$_4$ was very poor.

TABLE 3

| Run No. | DAM—CH$_3$Cl (mol %) | DAM—HCl (mol %) | DAM—H$_2$SO$_4$ (mol %) | DAM—(CH$_3$)$_2$SO$_4$ (mol %) | AA (mol %) | AN (mol %) | MA (mol %) | AM (mol %) | Viscosity at 25° C. (ps) | Isoelectric region (pH) | Thermal stability at 50° C. |
|---|---|---|---|---|---|---|---|---|---|---|---|
| 15 | 0.5 | — | — | — | 0.5 | — | — | 99 | 65 | None | Stable over 3 months or more |
| 16 | 20 | — | — | — | — | — | — | 80 | 50 | None | |
| 17 | — | — | — | — | 5 | — | — | 95 | 56 | None | |
| 18 | 50 | — | — | — | 50 | — | — | — | 4 | 4-10 | |
| 19 | — | 10 | — | — | 10 | — | — | 80 | 45 | 7-8 | Gelation after 1. week |
| 20 | — | — | 10 | — | 10 | — | — | 80 | 60 | 7-8 | Gelation after 3 days |
| 21 | — | — | — | 10 | 10 | — | — | 80 | 48 | 6-8 | Gelation |
| 22 | — | — | — | 10 | 10 | 20 | — | 60 | 55 | 6-8 | after 7 |

TABLE 3-continued

| Run No. | DAM—CH₃Cl (mol %) | DAM—HCl (mol %) | DAM—H₂SO₄ (mol %) | DAM—(CH₃)₂SO₄ (mol %) | AA (mol %) | AN (mol %) | MA (mol %) | AM (mol %) | Viscosity at 25° C. (ps) | Isoelectric region (pH) | Thermal stability at 50° C. |
|---|---|---|---|---|---|---|---|---|---|---|---|
| 23 | — | — | — | 10 | 10 | — | 5 | 75 | 40 | 6–8 | to 10 days |

Note:
DAM—HCl, DAM—H₂SO₄ and DAM—(CH₃)₂SO₄ indicate respectively the hydrochloride, sulfate and dimethyl sulfate-quaternized product of dimethylaminoethyl methacrylate.

EXAMPLE 5

A mixture of 14.0 g of DAM-CH₃Cl, 5.0 g of AA, 41.0 g of AM and 540 g of water was adjusted to pH 4 with 10 N sodium hydroxide and placed in a reactor equipped with a stirrer. After replacing oxygen in the reactor by nitrogen gas, 0.1 g of potassium persulfate was added thereto and polymerization was carried out at 45° C. for 7 hours to give a polymer solution. Conversion was 99.1%. The properties of the polymer solution were as follows: polymer content, about 10%; pH, 3.6; Brookfield viscosity (rotor No. 3; rotation, 12 rpm; 25° C.), 105 ps. From the polymer solution, a powder could be obtained in the same manner as in Example 1.

EXAMPLE 6

Various polymers were produced in the same manner as in Example 5 but varying the monomer compositions as shown in Table 4.

EXAMPLE 7

A mixture of 280 g of water, 128 g of acetone, 107 g of acrylamide, 6 g of DAM-CH₃Cl and 43 g of acrylic acid was neutralized with several drops of 1 N sodium hydroxide. The atmosphere in a reactor was replaced by nitrogen gas until it became oxygen-free, and 5 ml of 1% aqueous potassium persulfate solution and 5 ml of 2% aqueous sodium bisulfite solution were added thereto. Reaction began after several minutes and the viscosity increased with the progress of the reaction. Fifteen minutes after the viscosity-increase, a uniform solution of 117 g of DAM-CH₃Cl in 16 g of water was continuously added thereto over about 120 minutes. At the time when polymerization was advanced at 20° C. for about 80 minutes with stirring in a nitrogen stream, it reached the state where the Weissenberg phenomenon was about to appear. To decrease the viscosity of the reaction system, 8 g of acetone were gradually added, and the polymerization was allowed to proceed. Thereafter, the polymerization was advanced while controlling the viscosity of the reaction system with additions of 8 g of acetone every 0.5 to 1.5 hours so as to prevent the Weissenberg phenomenon and not to damage the Trommsdorf effect. Eight hours after the start of the reaction, 120 g of acetone were added to the reaction system, and after elevating the temperature to

TABLE 4

| Run No. | DAM—CH₃Cl (mol %) | AA (mol %) | AN (mol %) | MA (mol %) | MMA (mol %) | AM (mol %) | Viscosity at 25° C. (ps) | Isoelectric region (pH) | Thermal stability at 50° C. |
|---|---|---|---|---|---|---|---|---|---|
| 24 | 10 | 10 | — | — | — | 80 | 90 | 6–8 | |
| 25 | 10 | 10 | 20 | — | — | 60 | 100 | 6–8 | |
| 26 | 20 | 20 | — | — | — | 60 | 85 | 6–8 | |
| 27 | 10 | 10 | — | 5 | — | 75 | 80 | 6–8 | Stable over 3 months or more |
| 28 | 10 | 10 | — | — | 5 | 75 | 80 | 6–8 | |
| 29 | 2 | 2 | — | — | — | 96 | 120 | 6–7 | |
| 30 | 5 | 5 | — | — | — | 90 | 120 | 6–7 | |
| 31 | 5 | 15 | — | — | — | 80 | 105 | 5–6 | |
| 32 | 15 | 5 | — | — | — | 80 | 85 | 8–10 | |

Reference Example 2

Various polymers were produced in the same manner as in Example 5 but varying the compositions as shown in Table 5. The properties of the products are shown in Table 5.

TABLE 5

| Run No. | DAM—CH₃Cl (mol %) | DAM—HCl (mol %) | DAM—H₂SO₄ (mol %) | DAM—(CH₃)₂SO₄ (mol %) | AA (mol %) | AN (mol %) | AM (mol %) | Viscosity at 25°C. (ps) | Isoelectric region (pH) | Thermal stability at 50° C. |
|---|---|---|---|---|---|---|---|---|---|---|
| 33 | 0.5 | — | — | — | 0.5 | — | 99 | 150 | None | Stable over 3 or more |
| 34 | 20 | — | — | — | — | — | 80 | 80 | None | |
| 35 | — | — | — | — | 20 | — | 80 | 180 | None | |
| 36 | — | 10 | — | — | 10 | — | 80 | 90 | 7–8 | Gelation after 3 days |
| 37 | — | — | 10 | — | 10 | — | 80 | 95 | 7–8 | Gelation after 1 day |
| 38 | — | — | — | 10 | 10 | — | 80 | 80 | 6–8 | Gelation after 7 days |
| 39 | — | — | — | 10 | 10 | 20 | 60 | 90 | 6–8 | | about 40° C., 400 g of acetone was additionally added to deposits a polymer. The deposited powdery polymer was collected by filtration, washed with acetone several times and dried at 50° C. The product showed a good solubility in water. Polymerization yield, 98%. Brookfield viscosity (1% aqueous solution), 55 poise (25° C.; rotor No. 3, 12 rpm). Isoelectric region, pH 6 to 8. The thermal stability at 50° C. was examined, and no change was observed over 3 months or more. The resulting product was taken as the one in Run No. 40.

EXAMPLE 8

Waste paper pulp of corrugated paper was beat to a Canadian standard freeness of 400 cc and dispersed in water to obtain a 2% aqueous suspension. To the suspension, the polymer obtained in Example 2 or 4 or Reference Example 1 was added, and the pH was adjusted to 5.0 with alum for acidic sheeting or to 7.2 with sodium hydroxide and sulfuric acid for neutral sheeting.

Separately from this, a black liquor from the neutral sulfite semichemical process was concentrated (the solid components in the concentrate consisting of about 60% of sodium lignosulfonate, 20% of saccharides and 20% of inorganic salts) and added to the pulp liquor in an amount of 4% based on the bone dry weight of the pulp. The resulting pulp liquor was treated in the same manner as above.

Thereafter, the adjusted pulp liquor was sheeted by a Tappi standard machine to form a wet web having a basis weight of about 100 g/m². The web was dehydrated on a press at 3.5 kg/cm² for 5 minutes and dried into paper at 110° C. for 5 minutes. After the paper was stabilized at 20° C. for 24 hours in an atmosphere of 65% RH, the bursting strength was measured on a Müllen type bursting strength tester according to JIS (Japanese Industrial Standard) P-8112 to obtain a burst factor. The test results are shown in Table 6.

TABLE 6

| Polymer | Run No. | Black liquor not used | | Black liquor used | |
|---|---|---|---|---|---|
| | | pH of pulp liquor | | | |
| | | 5.0 | 7.2 | 5.0 | 7.2 |
| Examples 2 & 4 | 1 | 3.62 | 3.75 | 3.45 | 3.42 |
| | 2 | 3.35 | 3.42 | 3.30 | 3.26 |
| | 3 | 3.55 | 3.67 | 3.25 | 3.20 |
| | 4 | 3.64 | 3.82 | 3.52 | 3.37 |
| | 5 | 3.12 | 3.33 | 3.30 | 3.28 |
| | 6 | 3.58 | 3.72 | 3.31 | 3.24 |
| | 7 | 3.66 | 3.77 | 3.54 | 3.40 |
| | 8 | 3.68 | 3.86 | 3.55 | 3.58 |
| | 9 | 3.60 | 3.75 | 3.57 | 3.60 |
| | 10 | 3.62 | 3.70 | 3.45 | 3.43 |
| | 11 | 3.60 | 3.64 | 3.41 | 3.38 |
| | 12 | 3.56 | 3.58 | 3.35 | 3.38 |
| | 13 | 3.31 | 3.47 | 3.34 | 3.30 |
| | 14 | 3.45 | 3.51 | 3.33 | 3.34 |
| Reference Example 1 | 15 | 2.67 | 2.60 | 2.33 | 2.54 |
| | 16 | 3.03 | 3.07 | 2.65 | 2.53 |
| | 17 | 3.01 | 2.42 | 2.62 | 2.44 |
| | 18 | 2.53 | 2.50 | 2.35 | 2.40 |
| | 19 | 3.10 | 2.82 | 2.79 | 2.56 |
| | 20 | 3.07 | 2.76 | 2.81 | 2.45 |
| | 21 | 3.10 | 3.13 | 3.06 | 2.90 |
| | 22 | 3.15 | 3.15 | 3.08 | 2.98 |
| | 23 | 3.06 | 3.10 | 2.97 | 2.90 |
| No polymer | | 2.36 | 2.42 | 2.31 | 2.40 |

EXAMPLE 9

In order to clarify the physical properties of the polymers, paper was made with pulp liquors of varying pH, and the paper strength and the resin retention of the paper were measured. The results are shown in Table 7. The pulp liquor used was a 2% aqueous suspension of NBKP beat to a Canadian standard freeness of 450 cc, and the polymers used were those prepared in Examples 2 and 4 and Reference Example 1. The polymer was added to the pulp liquor in an amount of 0.6% based on the bone dry weight of pulp, and the liquor was adjusted to a required pH with alum, sulfuric acid or sodium hydroxide and sheeted in the same manner as in Example 7. The produced paper was tested for tensile strength and resin retention.

Tensile strength was measured on a Schopper tensile strength tester according to JIS P-8113 to obtain a breaking length. Resin retention was obtained by nitrogen analysis according to the Kjeldahl method.

TABLE 7

| Polymer | Run No. | Measurement item | pH = 4.5 | pH = 5 | pH = 7 | pH = 9 |
|---|---|---|---|---|---|---|
| Example 2 & 4 | 1 | Breaking length (km) | 9.35 | 9.52 | 9.70 | 9.40 |
| | | Resin retention (%) | 88.3 | 93.2 | 94.0 | 86.0 |
| | 8 | Breaking length | 9.64 | 9.86 | 9.66 | 9.65 |
| | | Resin retention | 89.2 | 95.2 | 94.7 | 84.2 |
| | 12 | Breaking length | 9.51 | 9.63 | 9.72 | 9.51 |
| | | Resin retention | 88.5 | 93.5 | 93.9 | 87.1 |
| Reference Example 1 | 16 | Breaking length | 7.86 | 8.37 | 8.67 | 8.53 |
| | | Resin retention | 53.4 | 73.8 | 77.2 | 78.6 |
| | 17 | Breaking length | 8.42 | 6.93 | 6.82 | — |
| | | Resin retention | 70.6 | 21.3 | 11.2 | — |
| | 19 | Breaking length | 8.01 | 8.13 | 7.51 | 6.72 |
| | | Resin retention | 70.0 | 74.1 | 63.3 | 30.7 |

TABLE 7-continued

| Polymer | Run No. | Measurement item | pH = 4.5 | pH = 5 | pH = 7 | pH = 9 |
|---|---|---|---|---|---|---|
| | 20 | Breaking length | 8.53 | 8.37 | 7.50 | 7.11 |
| | | Resin retention | 72.3 | 70.6 | 62.4 | 55.8 |
| | 21 | Breaking length | 8.44 | 8.95 | 8.98 | 8.50 |
| | | Resin retention | 76.2 | 79.8 | 78.5 | 72.5 |
| | 22 | Breaking length | 8.54 | 8.98 | 8.69 | 8.56 |
| | | Resin retention | 75.7 | 78.7 | 79.5 | 71.5 |
| No polymer | | Breaking length | 6.82 | 7.02 | 7.06 | 7.08 |

EXAMPLE 10

A 7% aqueous suspension of calcium carbonate was prepared. The polymers used in the foregoing examples were each added to the test liquor in an amount of 5 ppm (converted to the solid basis) based on the liquor, and a jar test was carried out. The results are shown in Table 8. The jar test was carried out as follows: the test liquor was stirred for 1 minute at 150 rpm and the size of the floc (floc diameter) was observed; after standing for 2 minutes, the turbidity of the supernatant liquor was measured (first cycle). Thereafter, two cycles of stirring and standing were carried out under the same conditions (second cycle, third cycle). As is apparent from Table 8, it was confirmed that the products of the present invention caused little or no breaking of flocs and no increase in turbidity of the supernatant liquor, although stirring increased in the order of the first, second and third cycles.

EXAMPLE 11

Thirty ppm of alum (converted to $Al_2O_3$ basis) was added to waste water (SS=86 ppm) from a kraft pulp process in a paper-making works, and the waste water was adjusted to varying pHs with sodium hydroxide or sulfuric acid. The flocculating ability of the polymers in the foregoing examples was measured according to the jar test using the waste water thus prepared. The results are shown in Table 9.

The amount of the polymer added was 0.5 ppm (converted to solid basis) based on the water to be treated. The jar test was carried out as follows: stirring was conducted for 1 minute at 150 rpm and the size of the floc (floc diameter) was observed; and after standing for 2 minutes, the turbidity of the supernatant liquor was measured. As is apparent from Table 9, the polymers of the present invention are hardly affected by the pH of the waste water. In practical waste water treatments, a stable operation is possible irrespective of the change of the property of the waste water.

TABLE 8

| Polymer | Run No. | First cycle Floc diameter[*1] | Turbidity[*2] | Second cycle Floc diameter[*1] | Turbidity[*2] | Third cycle Floc diameter[*1] | Turbidity[*2] |
|---|---|---|---|---|---|---|---|
| Examples 2, 4, 6 & 7 | 1 | $D_4$ | 10 | $D_{4-3}$ | 12 | $D_{4-3}$ | 12 |
| | 4 | $D_4$ | 9 | $D_4$ | 10 | $D_4$ | 9 |
| | 8 | $D_4$ | 9 | $D_4$ | 8 | $D_4$ | 9 |
| | 24 | $D_5$ | 7 | $D_{5-4}$ | 8 | $D_4$ | 9 |
| | 25 | $D_5$ | 5 | $D_5$ | 5 | $D_{5-4}$ | 6 |
| | 26 | $D_5$ | 5 | $D_5$ | 5 | $D_5$ | 5 |
| | 27 | $D_5$ | 7 | $D_6$ | 8 | $D_{5-4}$ | 8 |
| | 28 | $D_5$ | 7 | $D_5$ | 7 | $D_5$ | 8 |
| | 29 | $D_4$ | 12 | $D_4$ | 12 | $D_{4-3}$ | 15 |
| | 30 | $D_4$ | 13 | $D_{4-3}$ | 13 | $D_4$ | 13 |
| | 31 | $D_5$ | 12 | $D_{5-4}$ | 13 | $D_{5-4}$ | 15 |
| | 32 | $D_4$ | 8 | $D_5$ | 8 | $D_4$ | 8 |
| | 40 | $D_5$ | 4 | $D_5$ | 3 | $D_5$ | 4 |
| Reference Example 2 | 33 | $D_3$ | 45 | $D_{3-2}$ | 80 | $D_2$ | 120 |
| | 34 | $D_2$ | 38 | $D_2$ | 105 | $D_2$ | 231 |
| | 35 | $D_3$ | 74 | $D_2$ | 131 | $D_1$ | 275 |
| | 36 | $D_3$ | 24 | $D_3$ | 30 | $D_3$ | 50 |
| | 37 | $D_4$ | 20 | $D_3$ | 41 | $D_3$ | 77 |
| | 38 | $D_4$ | 15 | $D_4$ | 34 | $D_3$ | 51 |
| | 39 | $D_4$ | 10 | $D_{4-3}$ | 23 | $D_{4-3}$ | 35 |
| No polymer | | <$D_1$ | — | <$D_1$ | — | <$D_1$ | — |

Note:
[*1] Mean diameter of floc visually judged; e.g. $D_3$ means flocs of 3 mm in mean diameter.
[*2] According to JIS K-0101.

TABLE 9

| Polymer | Run No. | pH = 4.5 Floc diameter | Turbidity | pH = 6.0 Floc diameter | Turbidity | pH = 7.5 Floc diameter | Turbidity |
|---|---|---|---|---|---|---|---|
| Examples 6 & 7 | 24 | $D_5$ | 10 | $D_5$ | 10 | $D_5$ | 10 |
| | 25 | $D_5$ | 10 | $D_{4-5}$ | 10 | $D_5$ | 10 |
| | 26 | $D_5$ | 9 | $D_5$ | 10 | $D_5$ | 10 |
| | 29 | $D_4$ | 15 | $D_5$ | 15 | $D_4$ | 15 |
| | 30 | $D_4$ | 13 | $D_5$ | 14 | $D_5$ | 15 |
| | 31 | $D_5$ | 13 | $D_5$ | 13 | $D_5$ | 13 |
| | 32 | $D_4$ | 10 | $D_4$ | 10 | $D_4$ | 10 |
| | 40 | $D_5$ | 8 | $D_5$ | 7 | $D_5$ | 7 |
| Reference Example 2 | 33 | $D_3$ | 51 | $D_2$ | 55 | $D_1$ | 70 |
| | 34 | $D_2$ | 43 | $D_2$ | 45 | $D_1$ | 40 |
| | 35 | $D_2$ | 95 | $D_3$ | 90 | $D_3$ | 100 |
| | 36 | $D_3$ | 37 | $D_3$ | 35 | $D_2$ | 53 |
| | 37 | $D_3$ | 30 | $D_3$ | 38 | $D_2$ | 55 |
| | 38 | $D_4$ | 25 | $D_{4-3}$ | 30 | $D_{4-3}$ | 30 |
| No polymer | | $<D_1$ | — | $<D_1$ | — | $<D_1$ | — |

EXAMPLE 12

Supernatant liquor from digestion treatments of nightsoil waste water was diluted ten times with sea water and subjected to an activated sludge treatment. The polymers in the foregoing examples were each added to the surplus sludge (pH, 6.6; residue after evaporation, 48100 ppm; SS, 28000 ppm; $Cl^{-1}$, 8200 ppm) produced in the treatment in an amount of 200 ppm (converted to solid basis) based on the sludge. After thorough stirring, the sludge was dehydrated on a small centrifugal dehydrater, and the SS value of the filtrate and the water content of the dehydrated cake were examined. The results are shown in Table 10.

TABLE 10

| Polymer | Run No. | SS of filtrate (ppm) | Water content of dehydrated cake (%) |
|---|---|---|---|
| Example 6 & 7 | 24 | 50 | 80 |
| | 25 | 32 | 78 |
| | 26 | 25 | 78 |
| | 27 | 48 | 79 |
| | 28 | 45 | 78 |
| | 29 | 58 | 85 |
| | 30 | 50 | 83 |
| | 31 | 52 | 85 |
| | 32 | 39 | 80 |
| | 40 | 23 | 76 |
| Reference Example 2 | 33 | 208 | 90 |
| | 34 | 150 | 88 |
| | 35 | 330 | 95 |
| | 36 | 120 | 88 |
| | 37 | 105 | 87 |
| | 38 | 98 | 87 |
| | 39 | 90 | 85 |
| No polymer | | Not filterable | |

What is claimed is:

1. An amphoteric polyelectrolyte useful as a paper additive, a flocculant or a dehydrating agent, which is obtained by copolymerizing a vinyl monomer of the formula:

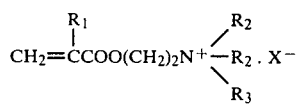 (I)

wherein $R_1$ is a hydrogen atom or a methyl group, $R_2$ and $R_3$ are each a methyl group or an ethyl group and X is a chlorine atom, a bromine atom or an iodine atom, a vinyl monomer of the formula:

 (II)

wherein M is a hydrogen atom, an alkali metal atom or an ammonium group and $R_4$ is a hydrogen atom or a methyl group and a vinyl monomer of the formula:

 (III)

wherein $R_5$ is a hydrogen atom or a methyl group, optionally with a vinyl monomer of the formula:

 (IV)

wherein $R_6$ is a hydrogen atom or a methyl group and $R_7$ is a phenyl group, —CN or —$COOR_8$ in which $R_8$ is methyl, ethyl, phenyl or —$(CH_2)_nOH$ wherein n is 2 or 3, the molar proportion of the vinyl monomers (I), (II), (III) and (IV) being 1 to 85:1 to 85:5 to 98:0 to 50, the reslting copolymer having a Brookfield viscosity of 1 poise or more when determined in a 10% by weight aqueous solution.

2. A process for producing an amphoteric polyelectrolyte useful as a paper additive, a flocculant or a dehydrating agent, which comprises copolymerizing a vinyl monomer of the formula:

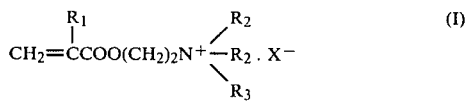 (I)

wherein $R_1$ is a hydrogen atom or a methyl group, $R_2$ and $R_3$ are each a methyl group or an ethyl group and X is a chlorine atom, a bromine atom or an iodine atom, a vinyl monomer of the formula:

 (II)

wherein M is a hydrogen atom, an alkali metal atom or an ammonium group and $R_4$ is a hydrogen atom or a methyl group and a vinyl monomer of the formula:

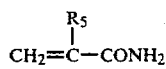
(III)

wherein $R_5$ is a hydrogen atom or a methyl group, optionally with a vinyl monomer of the formula:

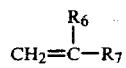
(IV)

wherein $R_6$ is a hydrogen atom or a methyl group and $R_7$ is a phenyl group, —CN or —COOR$_8$ in which $R_8$ is methyl, ethyl, phenyl or —(CH$_2$)$_n$OH wherein n is 2 or 3, in a solvent in the presence of a catalyst, the molar proportion of the vinyl monomers (I), (II), (III) and (IV) being 1 to 85:1 to 85:5 to 98:0 to 50, the resulting copolymer having a Brookfield viscosity of 1 poise or more when determined in a 10% by weight aqueous solution.

3. The process according to claim 2, wherein the solvent is water, a lower alkanol or a mixture of water and a water-miscible organic solvent.

4. The process according to claim 3, wherein the organic solvent is a lower alkanol, acetone, acetonitrile or dioxane.

5. The process according to claim 2, wherein the total concentration of the vinyl monomers (I), (II), (III) and (IV) in the solvent is from 5 to 80% by weight.

6. The process according to claim 2, wherein the catalyst is benzoyl peroxide, azoisobutyronitrile, ammonium persulfate, potassium persulfate, hydrogen peroxide or a redox catalyst comprising potassium persulfate and a member selected from the group consisting of sodium hydrogen sulfite, tertiary amines and sodium formaldehyde sulfoxylate.

7. The process according to claim 6, wherein the amount of the catalyst is about 0.01 to 1.0% by weight based on the total weight of the vinyl monomers (I), (II), (III) and (IV).

8. The process according to claim 2, wherein the vinyl monomer (I) is a quaternized compound having the formula:

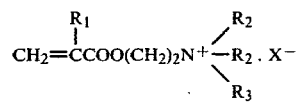

wherein $R_1$ is a hydrogen atom or a methyl group, $R_2$ is a methyl or ethyl group, $R_3$ is an ethyl group and X is a chlorine or bromine atom.

* * * * *